US010077352B2

(12) United States Patent
Funderburg et al.

(10) Patent No.: US 10,077,352 B2
(45) Date of Patent: Sep. 18, 2018

(54) POLYMERIC COMPOSITIONS WITH IMPROVED NOISE SUPPRESSION

(71) Applicant: Eastman Chemical Company, Kingsport, TN (US)

(72) Inventors: Michael Dean Funderburg, Gray, TN (US); Joseph Alexander DeLoach, Jonesborough, TN (US); Jesus Gabriel Moralez, Kingsport, TN (US); Philip Conrad Heidt, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 482 days.

(21) Appl. No.: 14/852,675

(22) Filed: Sep. 14, 2015

(65) Prior Publication Data
US 2016/0075856 A1  Mar. 17, 2016

Related U.S. Application Data

(60) Provisional application No. 62/050,942, filed on Sep. 16, 2014.

(51) Int. Cl.
| | |
|---|---|
| *C08K 5/11* | (2006.01) |
| *B05D 1/02* | (2006.01) |
| *F16F 15/02* | (2006.01) |
| *C08K 5/12* | (2006.01) |
| *C08K 5/103* | (2006.01) |
| *C07C 69/78* | (2006.01) |
| *C07C 69/75* | (2006.01) |
| *C07C 69/003* | (2006.01) |
| *C07C 63/06* | (2006.01) |
| *C08K 3/22* | (2006.01) |
| *C08K 3/26* | (2006.01) |

(52) U.S. Cl.
CPC ............... *C08K 5/103* (2013.01); *B05D 1/02* (2013.01); *C07C 63/06* (2013.01); *C07C 69/003* (2013.01); *C07C 69/75* (2013.01); *C07C 69/78* (2013.01); *C08K 3/22* (2013.01); *C08K 3/26* (2013.01); *C08K 5/11* (2013.01); *C08K 5/12* (2013.01); *F16F 15/02* (2013.01); *B05D 2518/00* (2013.01); *C08K 2003/2206* (2013.01); *C08K 2003/2296* (2013.01); *C08K 2003/265* (2013.01)

(58) Field of Classification Search
None
See application file for complete search history.

(56) References Cited

U.S. PATENT DOCUMENTS

| | | | |
|---|---|---|---|
| 4,102,862 A | 7/1978 | Monte et al. | |
| 4,346,782 A | 8/1982 | Böhm | |
| 4,584,215 A | 4/1986 | Bré et al. | |
| 5,387,753 A | 2/1995 | Scarlett et al. | |
| 5,686,553 A * | 11/1997 | Tai | C08G 63/20 264/176.1 |
| 5,741,824 A | 4/1998 | Butschbacher et al. | |
| 5,756,555 A | 5/1998 | Wesch et al. | |
| 6,559,213 B2 | 5/2003 | Wesch | |
| 7,524,896 B2 | 4/2009 | Kim et al. | |
| 8,088,446 B2 | 1/2012 | Billast | |
| 2004/0266927 A1 | 12/2004 | Prejean et al. | |
| 2006/0100366 A1* | 5/2006 | O'Brien | B65D 17/00 524/800 |
| 2006/0241197 A1 | 10/2006 | Arendt et al. | |
| 2007/0037926 A1 | 2/2007 | Olsen et al. | |
| 2009/0130316 A1 | 5/2009 | Billast | |
| 2009/0142981 A1 | 6/2009 | Arendt et al. | |
| 2010/0113664 A1 | 5/2010 | Bradshaw et al. | |
| 2011/0136940 A1* | 6/2011 | Evans | C08G 59/182 523/400 |
| 2012/0101225 A1 | 4/2012 | Kuo et al. | |
| 2015/0030770 A1* | 1/2015 | O'Brien | B65D 17/00 427/236 |
| 2015/0259497 A1 | 9/2015 | Mihara et al. | |
| 2016/0068629 A1* | 3/2016 | Lim | C08G 63/199 528/300 |
| 2016/0075855 A1 | 3/2016 | Funderburg et al. | |
| 2016/0075857 A1 | 3/2016 | Funderburg et al. | |
| 2016/0075858 A1 | 3/2016 | Funderburg et al. | |
| 2016/0122485 A1* | 5/2016 | Lim | C08J 5/18 525/444 |
| 2017/0335096 A1 | 11/2017 | Funderburg et al. | |

FOREIGN PATENT DOCUMENTS

| | | |
|---|---|---|
| CN | 103 483 957 A | 1/2014 |
| CN | 105 440 643 A | 3/2016 |
| EP | 0 416 822 A2 | 3/1991 |
| GB | 815 991 | 7/1959 |
| JP | 05 009355 A | 1/1993 |

(Continued)

OTHER PUBLICATIONS

USPTO Office Action dated Oct. 2, 2017 received in co-pending U.S. Appl. No. 14/852,662.
USPTO Office Action dated Sep. 1, 2016 received in co-pending U.S. Appl. No. 14/852,670.
USPTO Office Action dated Sep. 22, 2017 received in co-pending U.S. Appl. No. 15/159,165.
USPTO Notice of Allowance dated Dec. 6, 2017 received in co-pending U.S. Appl. No. 15/159,165.

(Continued)

*Primary Examiner* — Joseph D Anthony
(74) *Attorney, Agent, or Firm* — Kenrick L. Vidale

(57) ABSTRACT

Disclosed is a method for improving vibration damping of a substrate, such as the underbody of an automobile. The method comprises applying a plastisol which comprises a polymeric component and a plasticizer. The fused plastisol has improved damping behavior as determined using Dynamic Mechanical Thermal Analysis. Novel plastisols and novel plasticizers are also disclosed.

5 Claims, No Drawings

(56) References Cited

FOREIGN PATENT DOCUMENTS

| JP | 2000 169756 A | 6/2000 |
|---|---|---|
| JP | 2007 051303 A | 3/2007 |
| WO | WO 99/58597 A1 | 11/1999 |
| WO | WO 2008 011536 A2 | 1/2008 |
| WO | WO 2013 026918 A1 | 2/2013 |

OTHER PUBLICATIONS

Notification of Transmittal of the International Search Report and the Written Opinion of the International Searching Authority, or the Declaration; International Application No. PCT/US2017/031878 dated Jul. 26, 2017.

Funderburg, Michael; "The Effect of Plasticizers on Vibration Damping in Polyvinyl Chloride (PVC) Formulations" presentation for Society of Automated Engineers Noise and Vibration Conference and Exhibition in Grand Rapids, Michigan; Jun. 23, 2015.

Leventhall, Geoff; "Low Frequency Noise. What we know, what we do not know, and what we would like to know"; Journal of Low Frequency Noise, Vibration and Active Control, vol. 28, No. 2; pp. 79-104 (2009).

Society of Automated Engineers (SAE) Recommended Practice J1637-07, "Laboratory Measurement of Composite Vibration Damping Properties of Materials on a Supporting Steel Bar"; Jun. 2013.

Sperling, L. H. And Fay, J. J.; "Factors Which Affect the Glass Transition and Damping Capability of Polymers"; Polymers for Advanced Technologies, vol. 2; pp. 49-56; Oct. 1990.

Co-pending U.S. Appl. No. 14/852,662, filed Sep. 14, 2015 entitled Polymeric Compositions With Improved Noise Suppression; Funderburg et al.

Co-pending U.S. Appl. No. 14/852,670, filed Sep. 14, 2015 entitled Polymeric Compositions With Improved Noise Suppression; Funderburg et al.

Co-pending U.S. Appl. No. 14/852,681, filed Sep. 14, 2015 entitled Polymeric Compositions With Improved Noise Suppression; Funderburg et al.

Notification of Transmittal of the International Search Report and the Written Opinion of the International Searching Authority, or the Declaration dated Dec. 2, 2015 received in International Application No. PCT/US2015/050125.

Notification of Transmittal of the International Search Report and the Written Opinion of the International Searching Authority, or the Declaration dated Dec. 2, 2015 received in International Application No. PCT/US2015/050133.

Notification of Transmittal of the International Search Report and the Written Opinion of the International Searching Authority, or the Declaration dated Dec. 2, 2015 received in International Application No. PCT/US2015/050136.

* cited by examiner

POLYMERIC COMPOSITIONS WITH IMPROVED NOISE SUPPRESSION

CROSS-REFERENCE TO RELATED APPLICATION

This application claims priority to U. S. Provisional Application No. 62/050,942 filed Sep. 16, 2014, the disclosure of which is incorporated herein by reference in its entirety.

FIELD OF THE INVENTION

The invention relates to improving vibration damping on a substrate. More specifically, the invention relates to the use of plastisols to improve vibration damping on a substrate, such as the underbody of a vehicle. The invention also relates to novel plastisols and plasticizers for improving vibration damping.

BACKGROUND OF THE INVENTION

The objective of this invention is to provide improved vibration damping performance to metallic substrates. Examples of such substrates include, but are not limited to, those used for the construction of vehicles. More specifically, the objective of this invention is to provide improved vibration damping within the range of temperatures frequently encountered during driving, namely from −30° to 50° C. and most frequently from −10° C. to 40° C. Another objective of this invention is to provide improved vibration damping within this temperature range across the frequencies audible to humans, particularly in the low frequency range of 10 to 200 Hz as described in "Low Frequency Noise. What we know, what we do not know, and what we would like to know", Leventhall, Geoff, Journal of Low Frequency Noise, Vibration and Active Control 28, 2, pp. 79-104 (2009).

The reduction of noise, vibration, and harshness (often abbreviated as NVH) to humans is a goal of many industrial processes. Exposure to NVH comes from numerous sources, and can be mitigated by various means. For example, laminated safety glass can be comprised of acoustic interlayers which suppress sound transmission. Applications of such acoustic interlayers can include glass panes in commercial and residential buildings and automotive glazing. Other sources of NVH in vehicles include engine noise, road noise, springs and suspensions, braking, and chassis vibration. Noise suppression techniques include component design to reduce vibration and sound transmission; use of composite materials instead of metals; elastomeric sleeves or guards; nonwoven fabrics; carpet or other materials applied to the vehicle interior; foam; liquid-applied damping formulations; and objects produced from viscoelastic materials, such as bitumen or asphaltic pads. Although effective to varying extents depending on the source of the noise, these techniques suffer from limitations. For example, asphaltic pads cannot easily be placed and conformed to some locations on a vehicle body, require manual application, are subject to embrittlement, and must continue to adhere to the metal substrate in order to be effective. Some materials contribute undesired weight to the vehicle, contrary to weight reduction goals designed to improve fuel mileage. Materials which require high temperature and/or long times to cure can slow production, add cost, and result in higher energy usage.

One mode of NVH is through vibration. Polymeric materials can damp, or reduce oscillations of, a substrate by dissipating the oscillation energy with their viscoelastic behavior. A standard measurement of damping utilizes the Oberst method and apparatus. In this method, a material engineered to confer damping behavior is affixed to a stainless steel bar which has negligible damping itself. The effect of the damping material is deduced from the behavior of the sample bar compared to an untreated reference bar. Damping behavior may also be measured using Dynamic Mechanical Thermal Analysis, or DMTA. In this technique, a sample is exposed to a sinusoidal force, generally over a range of temperatures or frequencies. When heated, the modulus of a viscoelastic polymeric substance varies greatly from the glassy state at low temperatures, through the glass transition to a rubbery state, and finally to a lower viscosity molten state. The ratio of the storage modulus to the loss modulus, a value known as the tan δ, is a measure of the material's ability to damp vibrations. Higher tan δ values signify more effective damping behavior. The DMTA tan δ has been shown to correlate well with the Oberst bar testing.

Plasticized polyvinyl chloride (PVC) is well known in the automotive industry. Plasticized PVC applied as a plastisol in automotive underbody coatings and sealants, after thermal curing, can protect the vehicle from chipping by stones and other materials on the road surface. Such coatings also offer protection against corrosion, for example from salted roads. Plasticized PVC coatings can also provide a low level of reduction of the transmission of vibrations from metallic substrates. However, the performance of plasticized PVC coatings is inadequate to confer satisfactory vibration damping across the range of temperatures and noise frequencies typically encountered without the incorporation of additional damping techniques. These performance deficiencies are exacerbated when the desire to reduce NVH to vehicle passengers over traditional levels is considered. Despite these deficiencies, the ease of application and economy of PVC plastisols make them an appealing potential solution to the reduction of NVH should performance improvements be realized.

SUMMARY OF THE INVENTION

An embodiment is a plasticizer comprising the esterification product formed by the reaction of formula (I)

and formula (II)

or the corresponding esters, anhydrides, and/or acid chlorides of formula (I) and/or formula (II), with formula (III) and formula (IV)

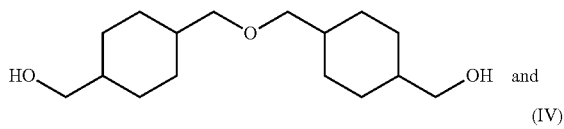

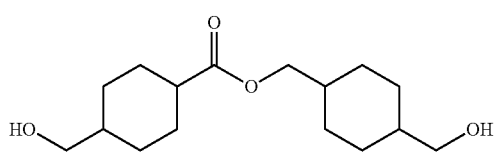

$R_1$ and $R_2$ are independently selected from the group consisting of phenyl, tolyl, cyclohexyl, 1-ethylpentyl, and methyl.

Another embodiment of the present invention is a plastisol comprising a polymeric component and a plasticizer. The plasticizer comprises the esterification product formed by the reaction of formula (I)

$$R_1COOH \qquad (I)$$

and formula (II)

$$R_2COOH \qquad (II)$$

or the corresponding esters, anhydrides, and/or acid chlorides of formula (I) and/or formula (II), with formula (III) and formula (IV)

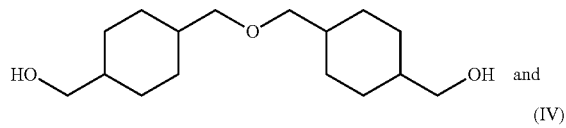

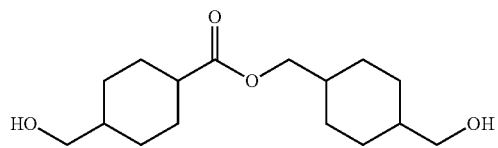

$R_1$ and $R_2$ are independently selected from the group consisting of an aromatic or alkyl-substituted aromatic group having 4 to 10 carbon atoms and a linear, branched, or cycloaliphatic alkyl group having 1 to 9 carbon atoms.

Yet another embodiment is a method of improving vibration damping of a substrate comprising affixing a plastisol onto a substrate. The plastisol comprises a polymeric component and a plasticizer. The plasticizer comprises the esterification product formed by the reaction of formula (I)

$$R_1COOH \qquad (I)$$

and formula (II)

$$R_2COOH \qquad (II)$$

or the corresponding esters, anhydrides, and/or acid chlorides of formula (I) and/or formula (II), with formula (III) and formula (IV)

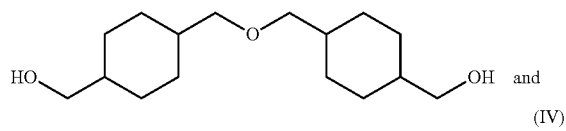

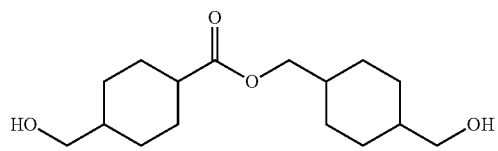

$R_1$ and $R_2$ are independently selected from the group consisting of an aromatic or alkyl-substituted aromatic group having 4 to 10 carbon atoms and a linear, branched, or cycloaliphatic alkyl group having 1 to 9 carbon atoms.

DETAILED DESCRIPTION OF THE INVENTION

As used herein the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The term "affixing", as used herein, refers to providing continuous and intimate contact between the plastisol and the substrate such that the fused plastisol remains on the substrate. For example, a plastisol can be affixed to a car underbody via spray coating the plastisol onto a car underbody and subjecting the coated car underbody to conditions to fuse the plastisol. The term "adhering" as used herein, refers to using an adhesive to affix a fused plastisol sheet to a substrate.

The term "esterification product", as used herein, refers to the blend of "partial esters", "mixed esters", and "diesters" produced from the reaction of one or more carboxylic acids with a diol. The term "partial esters", as used herein, refers to the reaction product wherein not all of the hydroxyls of a diol have fully reacted with a carboxylic acid. The term "mixed ester", as used herein, refers to the reaction product wherein each of the hydroxyls of a diol has reacted with different carboxylic acids. The term "diester", as used herein, refers to the reaction product wherein each hydroxyl of a diol has reacted with the same carboxylic acid. For example, if benzoic acid and toluic acid are reacted with 1-3-pentanediol, the esterification product can comprise the partial esters 1,3-pentanediol monobenzoate and 1,3-pentanediol monotoluate, the mixed ester 1,3-pentanediol benzoate/toluate, and the diesters 1,3-pentanediol dibenzoate and 1,3-pentanediol ditoluate. The term "the reaction product of formula (a) and formula (b) with formula (c)", as used herein, is intended to include carboxylic acids and the corresponding esters, anhydrides, and/or acid chlorides of formula (a) and/or formula (b) as explicitly set forth in the claims.

The term "plastisol", as used herein, refers to a liquid dispersion of polymeric resin particles, optionally with other ingredients, in a plasticizer. The term "fused plastisol", as used herein, refers to the solid plastic material that is formed upon fusing the plastisol and subsequently cooling to a desired temperature. The term "fusing", as used herein, refers to heating of the plastisol to a temperature sufficient to yield a solid structure with mechanical integrity.

The term "substrate", as used herein, refers to the material that provides the surface onto which the plastisol is affixed.

An embodiment is a plasticizer comprising the esterification product formed by the reaction of formula (I)

$$R_1COOH \qquad (I)$$

and formula (II)

$$R_2COOH \qquad (II)$$

or the corresponding esters, anhydrides, and/or acid chlorides of formula (I) and/or formula (II), with formula (III) and formula (IV)

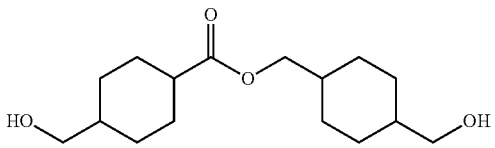

$R_1$ and $R_2$ are independently selected from the group consisting of phenyl, tolyl, cyclohexyl, 1-ethylpentyl, and methyl In one aspect, the ratio of phenyl to tolyl ranges from 0.05:20 to 20:0.05 based on the total amount of the esterification product. In other aspects, the ratio of phenyl to tolyl ranges from 0.1:10 to 10:0.1 or 0.1:5 to 5:0.1 or 0.5:1.5 to 1.5:0.5.

In one aspect, $R_1$ is phenyl and $R_2$ is methyl. In one aspect, $R_1$ and $R_2$ are the same.

One skilled in the art can readily make the above-identified plasticizers using process conditions well known in the art. For example, the proportions of mixed esters formed when two carboxylic acids are used may be adjusted by varying the ratios of the two carboxylic acids.

The esterification product formed by the reactions of the carboxylic acid(s) of formula (I) and formula (II) with the diol of formula (III) and formula (IV) can contain several reaction products including (1) partial esters formed when not all of the of the hydroxyls of formula (III) and formula (IV) are fully reacted with either formula (I) or formula (II), (2) mixed esters formed by the reaction of formula (I) with one hydroxyl of formula (III) and formula (IV) and formula (II) with the other hydroxyl of formula (III) and formula (IV) when $R_1$ and $R_2$ are different, and (3) diesters formed by the reaction of either formula (I) or formula (II) with both of the hydroxyls of formula (III) and formula (IV).

In one aspect, the plasticizer comprises the esterification product formula (V) and formula (VI)

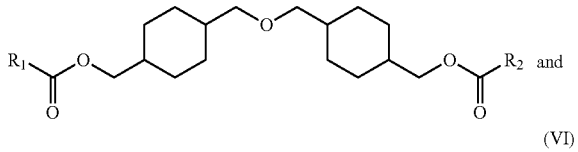

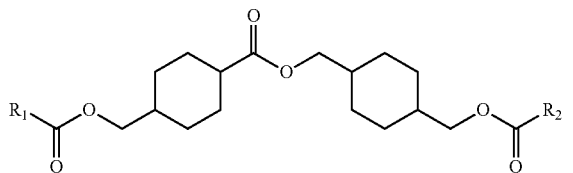

The esterification product comprises at least 10 weight percent of a mixed ester based on the total weight of the esterification product. Other examples of the amount of mixed ester based on the total weight of the esterification product include at least 15 weight percent, at least 20 weight percent, at least 25 weight percent, at least 30 weight percent, at least 40 weight percent, or at least 50 weight percent of a mixed ester. In one aspect, the amount of mixed ester ranges from 10 weight percent to 80 weight percent, 10 weight percent to 50 weight percent, 10 weight percent to 40 weight percent, 20 weight percent to 80 weight percent, 20 weight percent to 50 weight percent, or 20 weight percent to 50 weight percent, based on the total weight of the esterification product.

Another embodiment of the present invention is a plastisol comprising a polymeric component and a plasticizer. The plasticizer comprises the esterification product formed by the reaction of formula (I)

$$R_1COOH \tag{I}$$

and formula (II)

$$R_2COOH \tag{II}$$

or the corresponding esters, anhydrides, and/or acid chlorides of formula (I) and/or formula (II), with formula (III) and formula (IV)

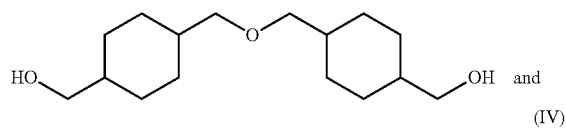

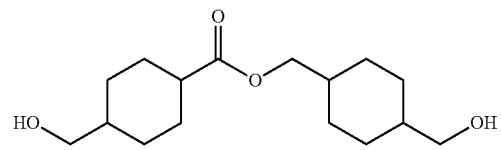

$R_1$ and $R_2$ are independently selected from the group consisting of an aromatic or alkyl-substituted aromatic group having 4 to 10 carbon atoms and a linear, branched, or cycloaliphatic alkyl group having 1 to 9 carbon atoms.

In one aspect, $R_1$ and $R_2$ are independently selected from the group consisting of phenyl, tolyl, cyclohexyl, 1-ethylpentyl, and methyl. In another aspect, $R_1$ is phenyl and $R_2$ is methyl. In one aspect, $R_1$ and $R_2$ are the same.

In one aspect, $R_1$ is phenyl, $R_2$ is tolyl, and the ratio of phenyl to tolyl ranges from 0.05:20 to 20:0.05 based on the total amount of the esterification product. In other aspects, the ratio of phenyl to tolyl ranges from 0.1:10 to 10:0.1 or 0.1:5 to 5:0.1 or 0.5:1.5 to 1.5:0.5.

In one aspect, the plasticizer comprises the esterification product formula (V) and formula (VI)

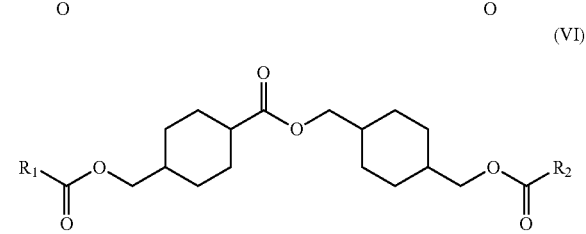

wherein the esterification product comprises at least 10 weight percent of a mixed ester, based on the total weight of the esterification product. Other examples of the amount of mixed ester based on the total weight of the esterification product include at least 15 weight percent, at least 20 weight percent, at least 25 weight percent, at least 30 weight percent, at least 40 weight percent or at least 50 weight percent of a mixed ester. In one aspect, the amount of mixed ester ranges from 10 weight percent to 80 weight percent, 10 weight percent to 50 weight percent, 10 weight percent to 40 weight percent, 20 weight percent to 80 weight percent, 20 weight percent to 50 weight percent, or 20 weight percent to 40 weight percent, based on the total weight of the esterification product In addition to the plasticizer, the plastisol comprises a polymeric component. In one aspect, the polymeric component comprises polyvinyl chloride, polyvinyl acetate, an acrylic polymer, and/or a vinyl chloride-containing copolymers. In one aspect, the polymeric component comprises polyvinyl chloride and/or an acrylic polymer. In one aspect, the polymeric component comprises polyvinyl chloride and/or polyvinyl acetate. In one aspect, the polymeric component comprises polyvinyl chloride and/or vinyl chloride-containing copolymers comprising vinyl acetate. In one aspect, the polymeric component comprises polyvinyl chloride and vinyl chloride-containing copolymers comprising acrylic. In one aspect, the polymeric component comprises polyvinyl chloride.

The plastisol comprises plasticizer, polymeric component, and other components. Examples of other components include, but are not limited to, a second plasticizer, fillers, pigments, stabilizers, foaming agents, hollow materials, elastomeric materials, rheology control additives, and adhesion promoters. The amounts of plasticizer, polymeric component, and other components can vary widely. For example, in one aspect the plastisol comprises 10 weight percent to 70 weight percent plasticizer, 10 weight percent to 70 weight percent polymeric component, and 10 weight percent to 80 weight percent other components, each based on the total weight of the plastisol. Other examples include, 15 weight percent to 60 weight percent plasticizer, 15 weight percent to 60 weight percent polymeric component, and 10 weight percent to 60 weight percent other components; or 20 weight percent to 45 weight percent plasticizer, 20 weight percent to 45 weight percent polymeric component, and 10 weight percent to 50 weight percent other components.

The viscosity of the plastisol can vary over a wide range. In one aspect, the plastisol has a viscosity ranging from 5,000 centipoise (cP) to 200,000 cP using Brookfield viscosity measurement at 23° C. In other examples, the plastisol has a viscosity ranging from 30,000 cP to 120,000 cP or from 40,000 cP to 90,000 cP.

In one aspect, the plastisol comprises a second plasticizer. In one aspect the second plasticizer comprises phthalates; terephthalates; isophthalates; trimellitates; adipates; cyclohexanedicarboxylates; benzoates; phosphates; diesters of ethylene glycol, propylene glycol, their oligomers, and mixtures thereof; citrates; succinates; alkyl sulfonates; fatty acid esters and epoxidized fatty acid esters; triglycerides and epoxidized triglycerides, optionally substituted; dianhydrohexitol diesters; pentaerythritol-based tetraesters; furan-based esters; other esters; ketals; and/or polymeric plasticizers. In another aspect, the second plasticizer comprises dioctyl terephthalate, diisooctyl phthalate, di-2-ethylhexyl phthalate, di-2-ethylhexyl terephthalate, tri-2-ethylhexyl trimellitate, di-2-propylheptyl phthalate, diisononyl phthalate, diisodecyl phthalate, diisoundecyl phthalate, ditridecyl phthalate, trioctyl trimellitate, triisononyl trimellitate, 2,2,4-trimethyl-1,3-pentanediol diisobutyrate, isononyl benzoate, isodecyl benzoate, diisononyl 1,2-cyclohexanedicarboxylate, dioctyl adipate, di-2-ethylhexyl adipate, triethylene glycol di-2-ethylhexanoate, diethylene glycol dibenzoate, dipropylene glycol dibenzoate, and/or dibenzoates produced from mixtures of diethylene glycol and dipropylene glycol. In one aspect, the second plasticizer comprises dioctyl terephthalate, di-2-ethylhexyl terephthalate, dioctyl adipate, di-2-ethylhexyl adipate, and/or triethylene glycol di-2-ethylhexanoate. In one aspect, the second plasticizer comprises, di-2-ethylhexyl terephthalate, diisononyl phthalate, and/or diisononyl 1,2-cyclohexanedicarboxylate.

In one aspect, the plastisol comprises fillers. Nonlimiting examples of fillers include calcium carbonate, magnesium carbonate, silica, clay, mica, graphite, zinc oxide, and calcium oxide. In one aspect, the fillers comprise calcium carbonate.

The plastisol, in one aspect, can comprise stabilizers. Nonlimiting examples of stabilizers include metal soaps, epoxidized oils and epoxidized fatty acid esters, and organotin compounds.

In one aspect, the plastisol can be formulated or produced in a manner which incorporates more free volume into the fused plastisol. In one such technique, mechanical frothing may be applied to produce a foamed plastisol. In another aspect, the plastisol can comprise a chemical foaming agent which results in a foamed structure after fusing is completed. One non-limiting example of such a foaming agent is azodicarbonamide. In one aspect, a catalyst is used along with the chemical foaming agent. In another aspect, foam stabilizers are used. In another aspect, hollow materials are incorporated into the plastisol. Nonlimiting examples of hollow materials include glass beads, microbeads, and/or microspheres, which can be produced from either inorganic or polymeric organic substances. In one aspect, the hollow materials are thermoplastic microspheres.

In one aspect, the plastisol comprises elastomeric materials. Nonlimiting examples of elastomeric materials include nitrile-butadiene rubber, natural rubber, isoprene rubber, butadiene rubber, styrene-butadiene rubber, butyl rubber, ethylene-propylene-diene monomer (EPDM) rubber, chloroprene rubber, styrenated block copolymers, ethylene-vinyl acetate copolymers, olefinic elastomers, olefinic copolymer elastomers, silicone elastomers, polysulfide elastomers, and/or polyurethane elastomers.

In another aspect, additives to control rheology can be incorporated into the plastisols. These may include secondary plasticizers or diluents. Examples of such additives include petroleum distillates; hydrocarbon oils such as, for example, mineral oil and mineral spirits; fatty acid esters; polyphenyl oligomers, optionally partially hydrogenated; and organic solvents. Conversely, thickeners may be added to boost viscosity as desired. Materials and techniques for adjusting plastisol rheology are well known in the art.

In one aspect, the plastisol comprises adhesion promoters. Nonlimiting examples of adhesion promoters include polyamidoamines, blocked isocyanates and isocyanurates, silanes, and/or epoxy resins.

In one aspect, the fused plastisol has a maximum Tan Delta (Tan $\delta_{max}$) occurring between 20° C. and 60° C. and has Tan Delta at 40° C. (Tan $\delta_{40\ C}$) ranging from 0.4 to 2.0, when measured on a sample nominally 0.6-0.7 mm thick, 3.2 mm wide, and 10-12 mm long using a Q800 Dynamic Mechanical Analyzer with a Tension Clamp at a strain of 0.1% and at a frequency of 1 Hz and a temperature ramp rate of 3° C./min.

In one aspect, Tan Delta at 30° C. (Tan $\delta_{30\ C}$) ranges from 0.4 to 1.8 or 0.4 to 1.6 or 0.4 to 1.4 or 0.6 to 2.0 or 0.6 to 1.8 or 0.6 to 1.6 or 0.6 to 1.4 or 0.7 to 2.0 or 0.7 to 1.8 or 0.7 to 1.6 or 0.7 to 1.4. In one aspect, Tan Delta at 40° C.

(Tan $\delta_{40\ °C}$) ranges from 0.4 to 1.8 or 0.4 to 1.6 or 0.4 to 1.4 or 0.6 to 2.0 or 0.6 to 1.8 or 0.6 to 1.6 or 0.6 to 1.4 or 0.7 to 2.0 or 0.7 to 1.8 or 0.7 to 1.6 or 0.7 to 1.4. In one aspect, the maximum Tan Delta (Tan $\delta_{max}$) occurs between 20° C. and 50° C. or 30° C. and 60° C.

Yet another embodiment is a method of improving vibration damping of a substrate comprising affixing a plastisol onto a substrate. The plastisol comprises a polymeric component and a plasticizer. The plasticizer comprises the esterification product formed by the reaction of formula (I)

R$_1$COOH    (I)

and formula (II)

R$_2$COOH    (II)

or the corresponding esters, anhydrides, and/or acid chlorides of formula (I) and/or formula (II), with formula (III) and formula (IV)

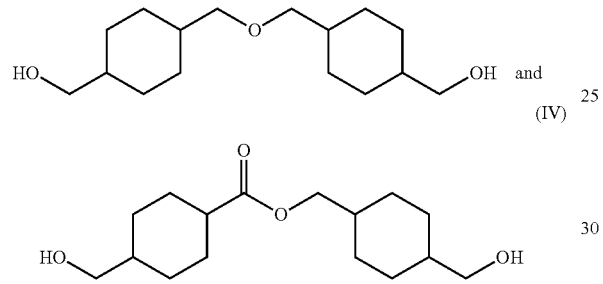

R$_1$ and R$_2$ are independently selected from the group consisting of an aromatic or alkyl-substituted aromatic group having 4 to 10 carbon atoms and a linear, branched, or cycloaliphatic alkyl group having 1 to 9 carbon atoms.

All of the aspects of the plastisol described herein above can apply to the method of improving vibration damping of a substrate. These aspects include the options for R$_1$ and R$_2$ groups, plasticizer, the amount of mixed esters, polymeric component, the amounts of plasticizer, polymeric component, and other components in the plastisol, plastisol viscosity ranges, second plasticizers, fillers, stabilizers, foaming agents, hollow materials, elastomeric materials, rheology control additives, adhesion promoters, maximum Tan Delta, Tan Delta at 30° C., and Tan Delta at 40° C.

The substrate is not particularly limited. In one aspect, the substrate is metal. In one aspect, the substrate comprises steel. In one aspect, the substrate comprises aluminum. In one aspect, the substrate is part of a wheeled vehicle. In another aspect, the substrate is on the underbody of a wheeled vehicle.

In one aspect, the method of affixing the plastisol onto the substrate comprises (a) applying the plastisol onto the substrate, (b) fusing the plastisol to produce a plastisol-covered substrate, and (c) cooling the plastisol-covered substrate to ambient temperatures. The method for applying the plastisol onto the substrate is not particularly limited. In one aspect, applying the plastisol onto the substrate comprises coating the substrate with the plastisol. Nonlimiting examples of coating include spray coating and/or extrusion coating.

In one aspect, the method of affixing the plastisol to the substrate comprises (a) fusing the plastisol into a sheet and (b) adhering the sheet to the substrate.

In one aspect, the fusing occurs at a temperature ranging from 100° C. to 220° C. for a time period ranging from 1 min to 2 hours. In another aspect, the fusing occurs at a temperature ranging from 140° C. to 180° C. for a time period ranging from 15 min. to 40 min.

Listed below are non-limiting embodiments

A1. A plasticizer comprising the esterification product formed by the reaction of formula (I)

R$_1$COOH    (I)

and formula (II)

R$_2$COOH    (II)

or the corresponding esters, anhydrides, and/or acid chlorides of formula (I) and/or formula (II), with formula (III) and formula (IV)

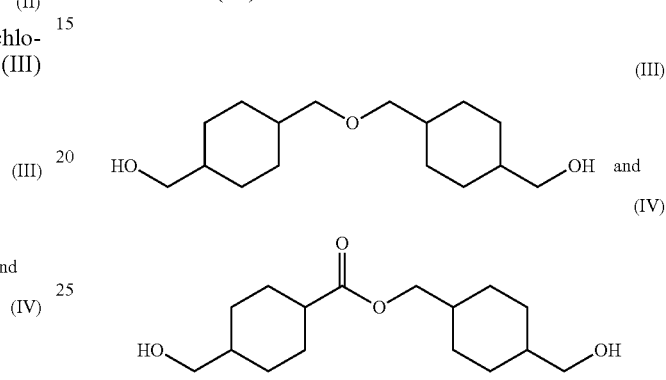

R$_1$ and R$_2$ are independently selected from the group consisting of phenyl, tolyl, cyclohexyl, 1-ethylpentyl, and methyl.

A2. The plasticizer according to embodiment A1, wherein R$_1$ is phenyl and R$_2$ is methyl.

A3. The plasticizer according to embodiment A1, wherein R$_1$ is phenyl, R$_2$ is tolyl, and the ratio of phenyl to tolyl ranges from 0.05:20 to 20:0.05 based on the total amount of said esterification product; or wherein the ratio of phenyl to tolyl ranges from 0.1:10 to 10:0.1 or 0.1:5 to 5:0.1 or 0.5:1.5 to 1.5:0.5.

A4. The plasticizer according to embodiment A1, wherein R$_1$ and R$_2$ are the same.

A5. The plasticizer according to any of embodiments A1-A3, wherein the plasticizer comprises the esterification product formula (V) and formula (VI)

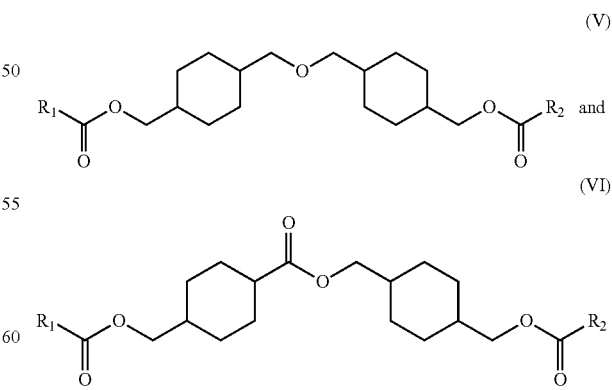

The esterification product comprises at least 10 weight percent of a mixed ester based on the total weight of the esterification product. Other examples of the amount of mixed ester based on the total weight of the esterification product include at least 15 weight percent, at least 20 weight percent, at least 25 weight percent, at least 30 weight percent, at least 40 weight percent, or at least 50 weight percent of a mixed ester.

B1. A plastisol comprising a polymeric component and a plasticizer. The plasticizer comprises the esterification product formed by the reaction of formula (I)

$$R_1COOH \qquad (I)$$

and formula (II)

$$R_2COOH \qquad (II)$$

or the corresponding esters, anhydrides, and/or acid chlorides of formula (I) and/or formula (II), with formula (III) and formula (IV)

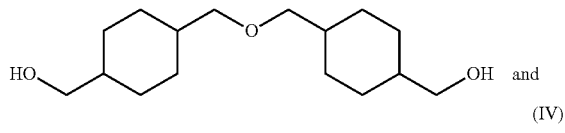

and

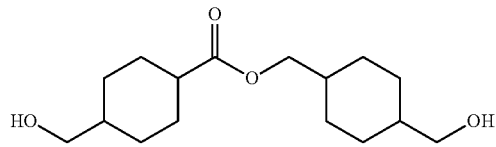

$R_1$ and $R_2$ are independently selected from the group consisting of an aromatic or alkyl-substituted aromatic group having 4 to 10 carbon atoms and a linear, branched, or cycloaliphatic alkyl group having 1 to 9 carbon atoms.

B2. The plastisol according to embodiment B1, wherein $R_1$ and $R_2$ are independently selected from the group consisting of phenyl, tolyl, cyclohexyl, 1-ethylpentyl, and methyl.

B3. The plastisol according to any of embodiments B1-B2, wherein $R_1$ is phenyl and $R_2$ is methyl.

B4. The plastisol according to any of embodiments B1-B2, wherein $R_1$ is phenyl, $R_2$ is tolyl, and the ratio of phenyl to tolyl ranges from 0.05:20 to 20:0.05 based on the total amount of the esterification product; or wherein the ratio of phenyl to tolyl ranges from 0.1:10 to 10:0.1 or 0.1:5 to 5:0.1 or 0.5:1.5 to 1.5:0.5.

B5. The plastisol according to any of embodiments B1-B2, wherein $R_1$ and $R_2$ are the same.

B6. The plastisol according to any of embodiments B1-B4, wherein the plasticizer comprises the esterification product formula (V) and formula (VI)

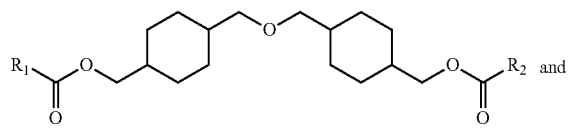

and

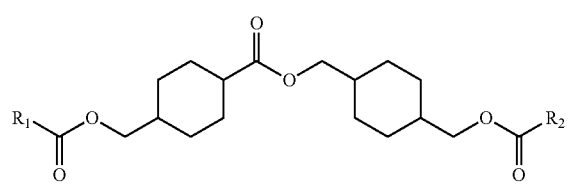

The esterification product comprises at least 10 weight percent of a mixed ester based on the total weight of the esterification product. Other examples of the amount of mixed ester based on the total weight of the esterification product include at least 15 weight percent, at least 20 weight percent, at least 25 weight percent, at least 30 weight percent, at least 40 weight percent, or at least 50 weight percent of a mixed ester.

B7. The plastisol according to any of embodiments B1-B6, comprising 10 weight percent to 70 weight percent of the plasticizer, 10 weight percent to 70 weight percent of the polymeric component, and 10 weight percent to 80 weight percent of other components, each based on the total weight of the plastisol, and wherein the other components comprise a second plasticizer, fillers, pigments, stabilizers, foaming agents, hollow materials, elastomeric materials, rheology control additives, and/or adhesion promoters; or 15 weight percent to 60 weight percent of the plasticizer, 15 weight percent to 60 weight percent of the polymeric component, and 10 weight percent to 60 weight percent of other components; or 20 weight percent to 45 weight percent of the plasticizer, 20 weight percent to 45 weight percent of the polymeric component, and 10 weight percent to 50 weight percent of other components.

B8. The plastisol according to any of embodiments B1-B7, wherein the polymeric component comprises polyvinyl chloride, polyvinyl acetate, acrylic polymers, and/or vinyl chloride-containing copolymers; or wherein the polymeric component comprises polyvinyl chloride.

B9. The plastisol according to embodiment B8, wherein the polymeric component comprises the polyvinyl chloride and the acrylic polymer; the polyvinyl chloride and the polyvinyl acetate; the polyvinyl chloride and the vinyl chloride-containing copolymers comprising acetate; or the polyvinyl chloride and the vinyl chloride-containing copolymers comprising acrylic.

B10. The plastisol according to any of embodiments B1-B9, wherein the plastisol has a viscosity ranging from 5,000 to 200,000 cP using Brookfield viscosity measurement at 23° C.; wherein the plastisol has a viscosity ranging from 30,000 to 120,000 cP; or wherein the plastisol has a viscosity ranging from 40,000 to 90,000 cP.

B11. The plastisol according to any of embodiments B7-B11, wherein the second plasticizer comprises phthalates; terephthalates; isophthalates; trimellitates; adipates; cyclohexanedicarboxylates; benzoates; phosphates; diesters of ethylene glycol, propylene glycol, their oligomers, and mixtures thereof; citrates; succinates; alkyl sulfonates; fatty acid esters and epoxidized fatty acid esters; triglycerides and epoxidized triglycerides, optionally substituted; dianhydrohexitol diesters; pentaerythritol-based tetraesters; furan-based esters; other esters; ketals; and/or polymeric plasticizers; or wherein the second plasticizer comprises dioctyl terephthalate, diisooctyl phthalate, di-2-ethylhexyl phthalate, di-2-ethylhexyl terephthalate, tri-2-ethylhexyl trimellitate, di-2-propylheptyl phthalate, diisononyl phthalate, diisodecyl phthalate, diisoundecyl phthalate, ditridecyl phthalate, trioctyl trimellitate, triisononyl trimellitate, 2,2,4-trimethyl-1,3-pentanediol diisobutyrate, isononyl benzoate, isodecyl benzoate, diisononyl 1,2-cyclohexanedicarboxylate, dioctyl adipate, di-2-ethylhexyl adipate, triethylene glycol di-2-ethylhexanoate, diethylene glycol dibenzoate, dipropylene glycol dibenzoate, and/or dibenzoates produced from mixtures of diethylene glycol and dipropylene glycol.

B12. The plastisol according to any of embodiments B7-B11, wherein the fillers comprise calcium carbonate, magnesium carbonate, silica, clay, mica, graphite, zinc oxide, and/or calcium oxide; or the fillers comprise calcium carbonate.

B13. The plastisol according to any of embodiments B7-B12, wherein the stabilizers comprise metal soaps, epoxidized oils and epoxidized fatty acid esters, and/or organotin compounds.

B14. The plastisol according to any of embodiments B7-B13, wherein the foaming agents comprise azodicarbonamide.

B15. The plastisol according to any of embodiments B7-B14, wherein the hollow materials comprise inorganic or organic glass beads, microbeads, and/or microspheres.

B16. The plastisol according to any of embodiments B7-B15, wherein the elastomeric materials comprise nitrile-butadiene rubber, natural rubber, isoprene rubber, butadiene rubber, styrene-butadiene rubber, butyl rubber, ethylene-propylene-diene monomer (EPDM) rubber, chloroprene rubber, styrenated block copolymers, ethylene-vinyl acetate copolymers, olefinic elastomers, olefinic copolymer elastomers, silicone elastomers, polysulfide elastomers, and/or polyurethane elastomers.

B17. The plastisol according to any of embodiments B7-B16, wherein the rheology control additives comprise petroleum distillates; mineral oil and mineral spirits; fatty acid esters; polyphenyl oligomers; and/or organic solvents.

B18. The plastisol according to any of embodiments B7-B17, wherein the adhesion promoters comprise polyamidoamines, blocked isocyanates and isocyanurates, silanes, and/or epoxy resins.

B19. The plastisol according to any of embodiments B1-B18, wherein the fused plastisol has a maximum Tan Delta (Tan $\delta_{max}$) occurring between 20° C. and 60° C. and has Tan Delta at 40° C. (Tan $\delta_{40\ C}$) ranging from 0.4 to 2.0, when measured on a sample nominally 0.6-0.7 mm thick, 3.2 mm wide, and 10-12 mm long using a Dynamic Mechanical Analyzer with a Tension Clamp at a strain of 0.1% and at a frequency of 1 Hz and a temperature ramp rate of 3° C./min.

B20. The plastisol according to embodiment B19, wherein the Tan Delta at 40° C. (Tan $\delta_{40\ C}$) ranges from 0.4 to 1.8 or 0.4 to 1.6 or 0.4 to 1.4 or 0.6 to 2.0 or 0.6 to 1.8 or 0.6 to 1.6 or 0.6 to 1.4 or 0.7 to 2.0 or 0.7 to 1.8 or 0.7 to 1.6 or 0.7 to 1.4.

B21. The plastisol according to any of embodiments B1-B209, wherein the Tan Delta at 30° C. (Tan $\delta_{30\ C}$) ranges from 0.4 to 1.8 or 0.4 to 1.6 or 0.4 to 1.4 or 0.6 to 2.0 or 0.6 to 1.8 or 0.6 to 1.6 or 0.6 to 1.4 or 0.7 to 2.0 or 0.7 to 1.8 or 0.7 to 1.6 or 0.7 to 1.4. B22. The plastisol according to any of embodiments B1-B21, wherein the maximum Tan Delta (Tan $\delta_{max}$) occurs between 20° C. and 50° C. or 30° C. and 60° C.

C1. A method of improving vibration damping of a substrate comprising affixing a plastisol according to any of embodiments B1-B21 onto a substrate.

C2. The method according to embodiment C1, wherein the affixing comprises (a) applying the plastisol onto the substrate; (b) fusing the plastisol to produce a plastisol-covered substrate; and (c) cooling the plastisol-covered substrate to ambient temperatures.

C3. The method according to embodiments C2, wherein the applying the plastisol onto the substrate comprises coating the substrate with the plastisol.

C4. The method according to embodiment C3, wherein the coating comprises spray coating and/or extrusion coating.

C5. The method according to embodiments C1, wherein the affixing comprises (a) fusing the plastisol into a sheet; and (b) adhering the sheet to the substrate.

C6. The method according to any of embodiments C2-C5, wherein the fusing occurs at a temperature ranging from 100° C. to 220° C. for a time period ranging from 1 min to 2 hours; or at a temperature ranging from 140° C. to 180° C. for a time period ranging from 15 min. to 40 min.

C7. The method according to any of embodiments C1-C6, wherein the substrate is part of a wheeled vehicle.

C8. The method according to embodiment C7, wherein the substrate is on the underbody of the wheeled vehicle.

EXAMPLES

The following plasticizers are commercially available and were used without further processing; Eastman 168™ Non-Phthalate Plasticizer (Comparative Example 1), Benzoflex™ 9-88 Plasticizer (Comparative Example 2) and Benzoflex™ 131 Plasticizer (Comparative Example 3) (Eastman Chemical Company, Kingsport, Tenn.), and Santicizer™ 278 Plasticizer (Comparative Example 4, Ferro Corporation, Mayfield, Ohio). All other ingredients used in the plastisols hereafter described are commercially available and were used without further processing.

Example 1

To a 2 liter round bottom flask equipped with an Oldershaw column and Dean-Stark trap was charged with a by-product from Eastman™ CHDM-D production containing 480 grams (1.78 moles) (oxybis(methylene)bis(cyclohexane-1,4-diyl))dimethanol, 256 grams (0.90 moles) (4-(hydroxymethyl)cyclohexyl)methyl 4-(hydroxymethyl)cyclohexanecarboxylate, and 64 grams (0.44 moles) 1,4-cyclohexanedimethanol; 776.7 grams (6.36 moles) benzoic acid; 1.00 grams zirconium carbonate; 0.50 grams tin oxalate; and 30 grams Isopar C, then the reaction mixture was heated to 210° C. with good stirring. At the end of the reaction, the mixture was cooled, diluted with tetrahydrofuran and washed with 10% sodium carbonate followed by washing with water. The mixture was dried with magnesium sulfate, filtered, and vacuum stripped to yield CHDM dimer dibenzoate (Example 1).

Example 2

To a 2 liter round bottom flask equipped with an Oldershaw column and Dean-Stark trap was charged with a by-product from Eastman™ CHDM-D production containing 240 grams (0.89 moles) ((oxybis(methylene)bis(cyclohexane-1,4-diyl))dimethanol, 128 grams (0.45 moles) (4-(hydroxymethyl)cyclohexyl)methyl 4-(hydroxymethyl)cyclohexanecarboxylate, and 32 grams (0.22 moles) 1,4-cyclohexanedimethanol; 458.2 grams (3.18 moles) 2-ethylhexanoic acid; 0.50 grams zirconium carbonate; 0.25 grams tin oxalate; and 30 grams Isopar C, then the reaction mixture was heated to 210° C. with good stirring. At the end of the reaction, the mixture was cooled, washed with 10% sodium carbonate followed by washing with water. The mixture was dried with magnesium sulfate, filtered, and vacuum stripped to yield CHDM dimer di-2-ethylhexanoate (Example 2).

Comparative Example 5

To a 250 milliliter round bottom flask equipped with a two-inch stainless steel mesh packed column and Dean- Stark trap was charged with 53.7 grams (0.37 moles) 1,3-cyclohexanedimethanol, 109.6 grams (0.76 moles) 2-ethylhexanoic acid, 0.06 grams zirconium carbonate, 0.03 grams tin oxalate, and 5.6 grams Isopar C, then the reaction mixture was heated to 200° C. with good stirring. At the end of the reaction, the mixture was cooled, washed with a solution of 10% sodium carbonate followed by washing with water. The mixture was dried with magnesium sulfate, filtered, and vacuum stripped to yield 1,3-CHDM di-2-ethylhexanoate (Comparative Example 5).

Preparation of PVC Formulations and Samples for DMTA Evaluation

Example 3

A FlackTek SpeedMixer™ model 150FV was used to prepare PVC plastisols. To a mixing cup was added 10 grams Geon™ 121A PVC paste resin, 4 grams Geon™ 217 PVC blending resin, 6 grams UltraPflex™ precipitated calcium carbonate, 0.4 grams calcium oxide, 0.2 grams zinc oxide, 1.0 grams Varsol 18™ Non-dearomatized Fluid, and 10 grams of CHDM dimer dibenzoate (Example 1). The contents were shaken in the mixer for 45 seconds and the side of the container was scraped. This process was repeated twice to ensure complete dispersion. The resulting plastisol was then deaerated in a desiccator to which vacuum was applied for 20 minutes.

Samples for DMTA analysis were prepared by drawdowns of the deaerated plastisols onto release paper at a 25 mil thickness, then fused at 350° F. for 25 minutes. Dynamic Mechanical Thermal Analysis (DMTA) measurements were performed on these samples using a tension clamp on a DMA Q800 from TA Instruments. Samples were cut using a ⅛ inch precision cutter, and sample width and thickness were recorded into the software. After loading the sample into the tension clamps, the software measured and recorded sample length. A 0.1% strain was placed on the sample at a 1 Hz frequency. The sample was then cooled with liquid nitrogen to −100° C. Once the temperature equilibrated, the sample was heated at a 3° C. per minute rate until a maximum of 100° C. was reached. Storage modulus, loss modulus, and tan δ results were recorded. Tan δ results at temperatures from −30° C. to 50° C., in 10° C. increments, are given in Table 1 b.

Example 4-Example 12

Example 3 was repeated, using the type and amount of plasticizer and the amount of Varsol rheology control additive as indicated in Table 1a. The correspondent tan δ results are given in Table 1 b.

TABLE 1a

Plastisols: 10 parts Geon ™ 121A, 4 parts Geon ™ 217, 6 parts UltraPflex ™, 0.4 parts calcium oxide, 0.2 parts zinc oxide, plasticizers and optionally Varsol ™ 18 rheology control additive as noted

| Example | Plasticizer Example | Parts Plasticizer | Parts Varsol |
|---|---|---|---|
| 3(a) | 1 | 10 | 3 |
| 4 | 2 | 10 | 2 |
| 5(a) | Blend of 1/Comparative Example 1 | 5/3 | 3 |
| 6 | Comparative Example 1 | 10 | 1 |
| 7 | Comparative Example 1 | 8 | 2 |
| 8(a) | Comparative Example 1 | 6 | 3 |
| 9(a) | Comparative Example 2 | 10 | 2 |
| 10(a) | Comparative Example 3 | 9 | 0 |
| 11(a) | Comparative Example 4 | 10 | 2 |
| 12(a) | Comparative Example 4 | 8 | 2.5 |
| 13 | Comparative Example 5 | 10 | 0 |

TABLE 1b

| | | Tan Delta (Tan δ) at given temperature (° C.) | | | | | | | | |
|---|---|---|---|---|---|---|---|---|---|---|
| Example | Plasticizer Example | −30 | −20 | −10 | 0 | 10 | 20 | 30 | 40 | 50 |
| 3(a) | 1 | 0.04 | 0.05 | 0.05 | 0.06 | 0.09 | 0.15 | 0.30 | 0.58 | 1.04 |
| 4 | 2 | 0.07 | 0.10 | 0.16 | 0.24 | 0.34 | 0.45 | 0.51 | 0.42 | 0.28 |
| 5(a) | Blend of 1/Comparative Example 1 | 0.05 | 0.07 | 0.09 | 0.13 | 0.20 | 0.31 | 0.45 | 0.58 | 0.52 |
| 6 | Comparative Example 1 | 0.16 | 0.21 | 0.26 | 0.31 | 0.37 | 0.40 | 0.36 | 0.27 | 0.19 |
| 7 | Comparative Example 1 | 0.12 | 0.15 | 0.18 | 0.22 | 0.26 | 0.32 | 0.37 | 0.36 | 0.29 |
| 8(a) | Comparative Example 1 | 0.07 | 0.09 | 0.11 | 0.14 | 0.18 | 0.23 | 0.29 | 0.36 | 0.39 |
| 9(a) | Comparative Example 2 | 0.03 | 0.05 | 0.10 | 0.19 | 0.31 | 0.45 | 0.61 | 0.55 | 0.29 |
| 10(a) | Comparative Example 3 | 0.11 | 0.13 | 0.14 | 0.16 | 0.18 | 0.20 | 0.21 | 0.19 | 0.17 |
| 11(a) | Comparative Example 4 | 0.04 | 0.05 | 0.08 | 0.14 | 0.25 | 0.45 | 0.70 | 0.74 | 0.41 |
| 12(a) | Comparative Example 4 | 0.04 | 0.05 | 0.06 | 0.09 | 0.15 | 0.27 | 0.49 | 0.74 | 0.59 |
| 13 | Comparative Example 5 | 0.15 | 0.20 | 0.24 | 0.28 | 0.31 | 0.33 | 0.33 | 0.29 | 0.22 |

For a limited number of the plastisols listed in Table 1a, the plastisol formulation was made a second time with the addition of 0.6 parts of Nourybond 272 (an adhesive promoter). These plastisols were subject to the Oberst bar method test.

The test was conducted as follows. Measurements were in accordance with the test method described in the SAE Recommended Practice J 1637-07, *Laboratory Measurement of Composite Vibration Damping Properties of Materials on a Supporting Steel Bar.*

The nominal dimensions of the steel bars were: mounted free length 200 mm, thickness 0.8 mm, and width 12.7 mm. Visco-elastic (damping) materials were bonded to this bar. Any excess material bonded to the bar was removed and cleaned, prior to installing the bar on the test set-up. The test temperatures that were used for this study were 10° C., 25° C., and 40° C.

Tests were made on a fixture to measure various modes of vibration that were generally between 100 Hz and 1000 Hz for each test bar using a random noise signal. The resonant frequency and the half power bandwidth (frequency difference between 3 dB down points from the resonant peak) of each mode needed for composite loss factor computation were read directly from a Pulse Multi-Analyzer System Type 3560. When the 3 dB down points on both sides of the resonant frequency were not measurable, the "n" dB down point method was used wherever possible per SAE Standard J1637-07.

The Oberst bar composite loss factors are shown as interpolated values at 200 Hz, 400 Hz, and 800 Hz for each temperature. These values are based on linear interpolation of two sets of data points where the frequency and the loss factor information are provided in a logarithmic scale. Should it not have been possible to interpolate data, then it was extrapolated. Results are shown in Table 2.

TABLE 2

| | Oberst bar composite loss factors | | | | | | | | |
|---|---|---|---|---|---|---|---|---|---|
| Plastisol Example | | | 3(b) | 5(b) | 8(b) | 9(b) | 10(b) | 11(b) | 12(b) |
| Oberst bar composite loss factors | Coating thickness, mm | | 2.1 | 1.9 | 2.2 | 2.3 | 2.0 | 2.5 | 1.8 |
| | 10° C. | 200 Hz | 0.100 | 0.059 | 0.045 | 0.085 | 0.040 | 0.119 | 0.068 |
| | | 400 Hz | 0.101 | 0.062 | 0.051 | 0.093 | 0.046 | 0.130 | 0.073 |
| | | 800 Hz | 0.105 | 0.066 | 0.056 | 0.117 | 0.044 | 0.155 | 0.089 |
| | 25° C. | 200 Hz | 0.071 | 0.046 | 0.040 | 0.036 | 0.026 | 0.069 | 0.047 |
| | | 400 Hz | 0.098 | 0.057 | 0.044 | 0.045 | 0.030 | 0.081 | 0.051 |
| | | 800 Hz | 0.083 | 0.052 | 0.051 | 0.058 | 0.034 | 0.115 | 0.073 |
| | 40° C. | 200 Hz | 0.018 | 0.018 | 0.030 | 0.012 | 0.013 | 0.017 | 0.019 |
| | | 400 Hz | 0.024 | 0.022 | 0.035 | 0.015 | 0.015 | 0.021 | 0.020 |
| | | 800 Hz | 0.032 | 0.029 | 0.039 | 0.020 | 0.018 | 0.031 | 0.028 |

Other embodiments will be apparent to those skilled in the art from consideration of the specification and practice of the embodiments disclosed herein. It will be understood that variations and modifications can be effected within the spirit and scope of the disclosed embodiments. It is further intended that the specification and examples be considered as exemplary only, with a true scope and spirit of the disclosed embodiments being indicated by the following.

We claim:

1. A plasticizer comprising the esterification product formed by the reaction of formula (I)

R$_1$COOH     (I)

and formula (II)

R$_2$COOH     (II)

or the corresponding esters, anhydrides, and/or acid chlorides of formula (I) and/or formula (II), with formula (III) and formula (IV)

(III)

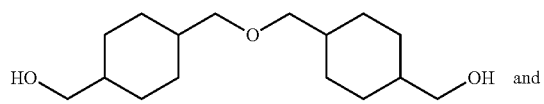

and

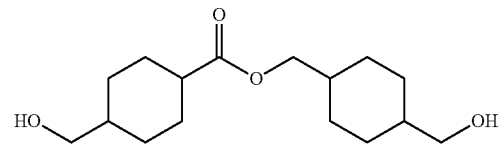

(IV)

wherein R$_1$ and R$_2$ are independently selected from the group consisting of phenyl, tolyl, cyclohexyl, 1-ethylpentyl, and methyl.

2. The plasticizer according to claim 1, wherein R$_1$ is phenyl and R$_2$ is methyl.

3. The plasticizer according to claim 1, wherein the ratio of phenyl to tolyl ranges from 0.05:20 to 20:0.05 based on the total amount of said esterification product.

4. The plasticizer according to claim 1, wherein R$_1$ and R$_2$ are the same.

5. The plasticizer according to claim 1, wherein said plasticizer comprises said esterification product formula (V) and formula (VI)

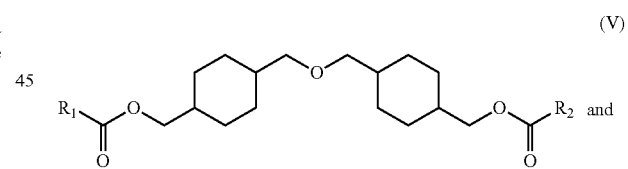

(V)

and

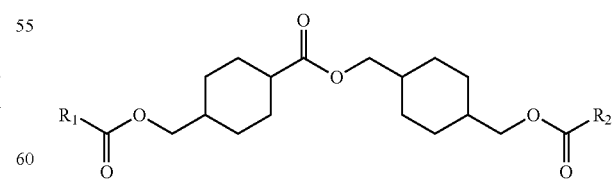

(VI)

and wherein said esterification product comprises at least 10 weight percent of a mixed ester, based on the total weight of said esterification product.

* * * * *